United States Patent [19]
Parker, Jr.

[11] Patent Number: 5,546,696
[45] Date of Patent: Aug. 20, 1996

[54] ANIMAL TRAP COMPOSITE BAIT MATERIAL AND METHODS OF USE

[76] Inventor: Kenneth B. Parker, Jr., 23516 Bell Bluff Truck Trail, Alpine, Calif. 91901

[21] Appl. No.: 294,411

[22] Filed: Aug. 22, 1994

[51] Int. Cl.⁶ .......................... A01M 23/00; A01M 23/24
[52] U.S. Cl. ........................................ 43/58; 43/81; 426/1
[58] Field of Search ............................. 426/1; 43/58, 81, 43/82, 94, 81.5, 77, 94, 88, 92; 424/84, 407, 420

[56] References Cited

U.S. PATENT DOCUMENTS

| | | | |
|---|---|---|---|
| 1,366,509 | 1/1921 | Thlessen | 426/1 |
| 1,608,688 | 11/1926 | Williamson | 426/1 |
| 2,595,019 | 4/1952 | Sullivan | 426/1 |
| 4,514,960 | 5/1985 | Sears | 424/84 X |
| 4,681,758 | 7/1987 | Fruthaler et al. | 424/84 X |
| 4,803,799 | 2/1989 | Vajs et al. | 43/82 |
| 4,990,514 | 2/1991 | Bruey | 424/84 X |
| 5,017,620 | 5/1991 | Grassman et al. | 424/48 X |

OTHER PUBLICATIONS

*The Washington Post*, "Hot Housewares . . .", Jan. 24, 1991, Thur. Final Edition, Home Section.
*In Health*, "Tiny Game Hunting", by Klein, Hilary D., pp. 72–75, Jul.–Aug. 1991.
*The Reuter Library Report*, "Mousetraps Still A Source of Human Fascination", by Hayley, Julia, Oct. 1990.
The House Mouse: Its Biology and Control, University of California, Division of Agrigultural Sciences, Rex E. Marsh and Watter E. Howard, pp. 5–31, Aug. 1981.
Bait additivies as a means of improving acceptance by rodents; R. E. Marsh, Sep. 7–11, 1987, pp. 195–202, paper presented to EPPO Conference on Rodents, Rome.
Pheromones (Odors) for Rodent Control? by Rex E. Marsh and Walter E. Howard, Pest Control Technology, Jun., 1979.
Principles and Techniques of Formulating Effective Rodent Baits—Present and Future, Rex E. Marsh, Proceedings of the Second Symposium on Recent Advances in Rodent Control, Kuwait, 1986.
Advertisement from Wildlife Control Technology, Sep.–Oct. 1994 edition by Rob Erickson, of Glendale Hts., IL.
Advertisement for Wildlife Control Technology, Sep.–Oct. 1994 edition by Jameson's Ultra Blend of Brownsville, PA.

*Primary Examiner*—J. Elpel
*Attorney, Agent, or Firm*—Fulwider Patton Lee & Utecht

[57] ABSTRACT

Improved animal bait composite materials comprising an animal attractant substance component attractive to a selected animal and a hardening substance component, and methods of use of such bait composite materials are described. The bait composite materials disclosed having improved adhesion and interlocking properties when hardened after application to a trigger of an animal trap in a flowable state, resulting in more reliably transferring forces applied by the bite or other contact of a selected animal to the trigger to actuate the trap.

7 Claims, 2 Drawing Sheets

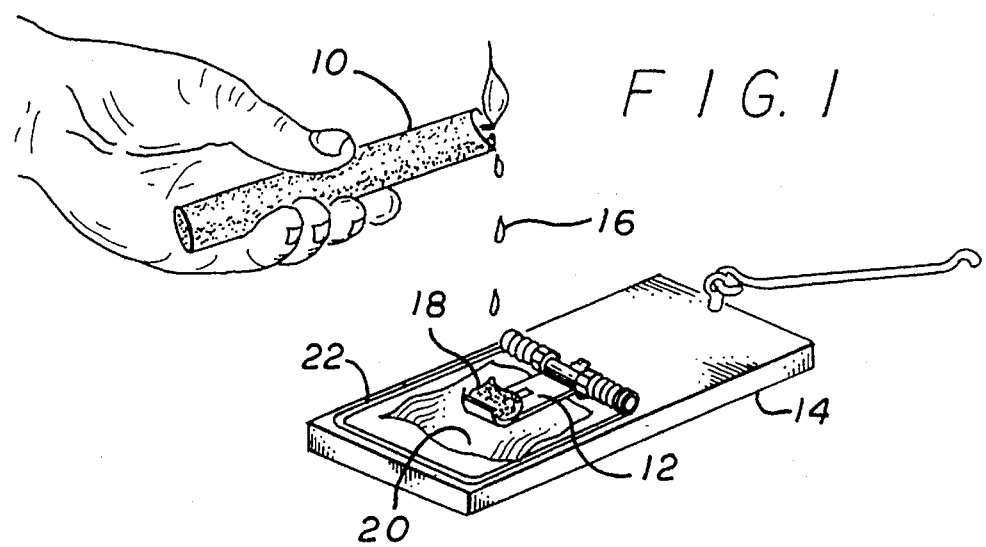
FIG. 1
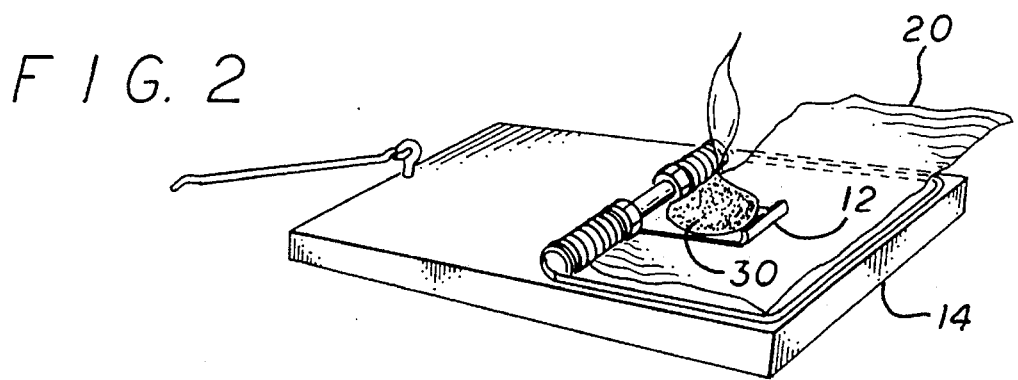
FIG. 2
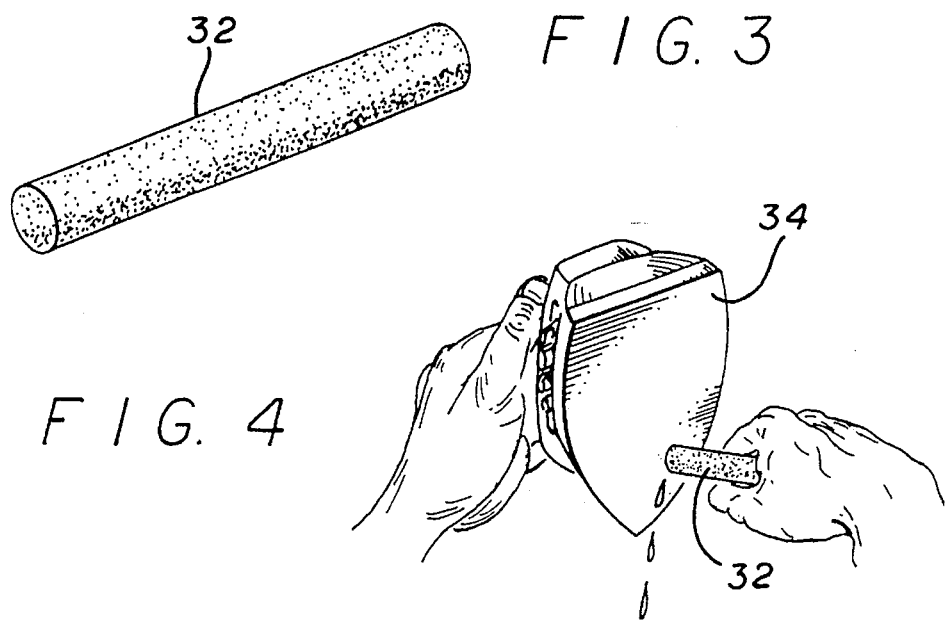
FIG. 3
FIG. 4

ANIMAL TRAP COMPOSITE BAIT MATERIAL AND METHODS OF USE

BACKGROUND OF THE INVENTION

1. Field of the Invention

This invention relates generally to baits for attracting selected animals to animal traps for capture in trapping to control selected animal populations. More particularly, the invention concerns a composite bait material attractive to a selected animal which is applied to a trap actuating trigger, and which is intended to adhere thereto.

2. Description of Related Art

The need for controlling certain animal populations, for example, rodents, in areas used by humans or livestock, or in the locale of stored food, has been recognized for centuries. In the case of rats and mice, serious health issues surround the proximity of these animals and humans and livestock due to infectious agents borne by the animals and the parasites infesting them. The long history of attempts at control of selected animal populations and the many poisons and varieties of traps invented for this purpose attest to the concern felt by humans and the effort allocated to solving this problem.

Poisoning may be the most common method of animal population control, but it has several disadvantages, particularly in a household setting, although also in agricultural or commercial applications. Poisons placed for consumption by mice or rats, for example, may be consumed by other animals including household pets, causing their unintended illness or death. In a similar way, mice or rats that consume poison may, after death, be eaten by other animals or pets, again causing illness or death due to ingestion of the poisoned mouse or rat.

Use of poisons, in addition to potential harm to animals not selected for control, has the additional significant disadvantage of being hazardous to humans. Particularly, small children are at a risk as they may play with, absorb or consume poison left for mice and rats.

A third disadvantage with the use of poison is the unpleasant odor resulting after a mouse or rat, for example, has been successfully poisoned. It is most common that the poisoned mouse or rat will die in a confined location, such as within the walls of a home or in the attic space. In such situations, it is usually impractical to locate and remove the dead animal. As a result, odor associated with decay may last for many days, making living within such a home very unpleasant.

In addition to poisons a variety of mechanical traps are currently employed in animal population control. The most common for use in trapping rodents is the spring operated version which, when triggered, causes a stiff metal wire to strike and kill the mouse or rat.

A second type of trap which has become popular in the past several years is the "sticky trap", consisting of a flat tray containing a jelly like plastic material whose surface remains very tacky or sticky. With this type of trap, the mouse or rat adheres to the surface when it walks on to the trap. This trap has the disadvantage that it does not quickly kill the mouse or rat, leaving this unpleasant task to be addressed by the user and causing the animal caught in the trap to remain in that condition for the period of time until the trap is detected.

Because of the disadvantages of poisons and sticky traps, mechanical traps of the spring loaded variety are widely used. With these traps, it is necessary to bait the trigger with something that will attract the mouse or rat.

One of the difficulties encountered in such trapping is removal of the bait from the trap by an animal without actuating the trigger of the trap, thereby rendering the trap ineffectual. This "stealing" of the bait by the animal can be a significant factor lessening the success of population control efforts.

For example, cheese has been commonly thought to be a food substance attractive to rodents, and appears to be in common use for this purpose today. However, it is known that cheese, while it may initially adhere to a trigger of a trap, rapidly dries and in so doing contracts and exudes oily substances, impairing adhesion, and making stealing of the bait without actuation of the trap trigger more likely.

It has been recognized by those skilled in the art that there are much more effective food substances than cheese to attract rodents, for example grains, and other seeds and nut-fruit of a variety of plants. However, getting such substances to adhere to a trap trigger is problematic. One approach has been to use peanut butter. This adheres well initially, but is so soft that forces applied to the peanut butter by the chewing rodent, which otherwise may actuate the trigger, are not transferred thereto. As peanut butter becomes harder, it tends to transfer chewing forces better, but it also tends to contract and exude oils which can considerably lessen the adhesion of this bait substance to the trigger of a trap. Again, this may result in diminished success in trap triggering and hence less success in animal population control.

In selecting a bait for the trigger of mechanical traps, several factors are important. First, the bait must be something that will attract the mouse or rat. Next, the bait must be able to be attached securely to the trigger so that it cannot be removed without triggering the trap. Next, the bait must be rather solid so that it cannot be eaten without triggering the trap.

Substances that are known to attract mice and rats include meat and fish, some vegetables and legumes (such as alfalfa) in addition to the grains, nuts and seeds mentioned. As previously noted, many people use cheese.

The triggers on mechanical traps for rodents have various configurations depending on the manufacturer. Some have an opening to accept and contain the bait. Others have a blade shape for penetration of the bait. These configurations are generally not very successful when attaching hard baits such as grains or nuts. Also, they do not successfully retain softer baits, thus allowing the easy stealing of baits such as meats, cheese or peanut butter.

Another consideration in trapping to control a population of a selected animal is the ease of baiting the trap and convenient handling of baited trap. Frequently, in attempting to control an animal population with mechanical traps many traps must be set. It is important in such circumstances, that a reliable method of baiting the traps without being unduly difficult or time-consuming be used. Furthermore, it may be most convenient to bait all traps to be set at one time in one location, then distribute the baited traps to the various desired locations and then set them. if this latter procedure is adopted, great care must be taken not to detach the bait when moving a baited trap to its new location to be set. Bait knocked off the trigger during transport must be replaced, and this, of course, is very inconvenient.

These examples illustrate the difficulties encountered in baiting traps to attract a selected animal and also minimize the occurrence of bait stealing. In light of the forgoing, it has been recognized that the desirable attributes of mechanical animal trap bait includes easy application to the trigger, and reliable and secure retention by an adhesion to the trigger of a trap, as well as stiffness to transfer forces from bites taken and other contact by an animal to the trigger for reliable trap actuation. Also, to increase trapping success, the most attractive substances to a selected animal to be trapped theoretically should be incorporated in the bait, even though they do not of themselves offer adhesive properties or other properties useful in addressing the aforementioned problems.

Those skilled in the art will appreciate that a bait substance of increased effectiveness will be easy to apply to a trap trigger, strongly attract the selected animal reliably transfer forces to the trigger of a trap and also be securely retained thereby and adhere thereto, to prevent bait stealing, without loss of its animal attractant function. The present invention addresses these concerns.

SUMMARY OF THE INVENTION

Briefly, and in general terms, the present invention provides an improved animal trap composite bait material including an animal attractant food substance and a hardening substance. The animal attractant is chosen based upon the particular application (animal species desired to be trapped). The hardening substance is selected so as to assume a solid state in the environment at which the trap is to be located. More particularly, the temperature range and humidity to be encountered at the location of a trap with which the composite bait material is to be used may affect the hardening substance chosen for a particular application. The hardening substance then acts as a matrix to support and bind together dispersed attractive food substance, as well as attach a mass of such attractive food substance to said trigger.

The composite bait material is flowable when applied to a trigger of a trap, so as to flow into and around the geometry of the trigger. After a short time the hardening substance transforms to a solid and the composite bait material adheres to, and mechanically interlocks with, the trigger to provide improved force transfer from an animal biting the hardened bait to the trigger and decrease the likelihood of bait stealing by an animal.

In a more detailed aspect, a composite bait material of the invention may be made to transition from a flowable to a hardened state in a number of ways. For example, the composite may include a hardening substance which can be heated to transform it to a liquid phase, making the composite bait material flowable, then harden as it cools back to ambient temperature.

In a further more detailed aspect, hardening substances that change from a liquid to solid state due to the evaporation of a solvent contained therein or colloidal fluid in which an adhesive is suspended may be used. Likewise substances which react chemically with moisture or some other component in the environment of the trap to harden could be used, as well as substances that cure after mixing two or more substances by some manipulation, for example, those that are mixed just prior to the time the bait is applied to the trigger, such as epoxy and hydrating cements.

In another more narrow aspect, the attractant substance may conveniently comprise a milled food substance favored by the selected animal to be trapped, for example particles of nuts and grains or other seeds in the case of rodents. Such a substance interacts with the hardening substance to be flowable when the hardening substance is in a liquid state, and thereafter form a hardened mass after the composite bait material is applied to the trigger and the hardening substance changes to a solid state, giving the desired stiffness and adhesion properties to interlock with, and firmly adhere to said trigger.

Other features and advantages of the invention will become apparent from the following detailed description, taken in conjunction with the accompanying drawings, which illustrate, by way of example, the features of the invention.

DESCRIPTION OF THE DRAWINGS

FIG. 1 is a perspective view of a trap being baited with an embodiment of the bait composite of the invention;

FIG. 2 is a perspective view of another embodiment of the invention;

FIG. 3 is a perspective view of a further embodiment of the composite bait material of the invention;

FIG. 4 is a perspective view of another embodiment wherein the composite bait material is heated without flame;

DETAILED DESCRIPTION OF THE PREFERRED EMBODIMENTS

Figure 5:
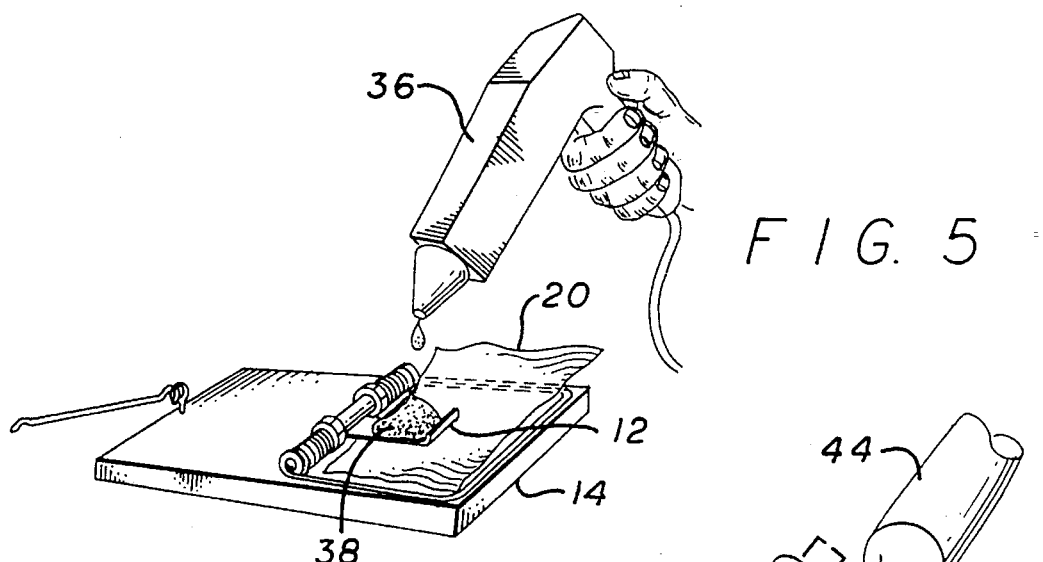
FIG. 5 is a perspective view of a further embodiment where hot bait is applied to a trap without flame.

As shown in FIG. 1 of the drawings, which are provided for purposes of exemplary illustration, the invention in one embodiment comprises a candle 10 which is formed of a composite bait material of an attractant food substance in particulate form and a hardening substance acting as a binder, which is a solid at ambient temperature, but which liquifies when the candle is lit. The composite bait material is applied to a trigger 12 of a trap 14 by lighting the candle, and allowing the melted and now liquified composite bait material 16 to drip onto the trigger. The composite bait material flows around and conforms to the shape and irregularities of the trigger and subsequently hardens, forming a mass of composite bait material 18 adhering to, and interlocking with, the geometry of the trigger 12.

A piece of paper 20 may be placed underneath the trigger 12 to catch any excess composite bait material that does not adhere to the trigger. The paper is removed after the composite bait material 18 has been applied to the trap 14. A coated or "glossy" paper or wax paper has been found to work well for this purpose.

The trap is then set, for example in the illustrated embodiment by conventionally folding back a spring-loaded U-shaped wire 22, and thereafter interlocking a retaining wire 24 and the trigger 12 to hold the spring-loaded U-shaped wire in place. When the trigger is moved, such movement releases the retaining wire and allows the U-shaped wire to snap back to the original position as is well known is the art.

It is preferable that this triggering of the trap 14 be done by an animal sought to be caught, and not the human user, hence the composite bait material 18 is applied prior to setting the trap. Depending on the sensitivity of the trigger 12, it may, however, be possible to freshen the bait of a previously set trap without releasing the spring loaded U-shaped wire 22 when employing the composite bait material of the invention in this embodiment. Because the composite bait material is merely dripped upon the trigger, additional bait may be applied to a previously baited and set trap, without contact with the trigger by the user. A paper 20 may be gently placed under the trigger without touching it and the candle of composite bait material placed above the trigger, beyond the reach of the spring-loaded wire 22. After sufficient liquified composite bait material 16 is dripped onto the trigger 12, the paper (with any excess composite bait material thereon) is removed, completing the freshening of the bait.

According to the invention, the candle 10 is formed of composite bait material. The composite bait material is a mixture of a hardening substance which acts as a binder, and an animal attractant substance in particulate form. The hardening substance in the illustrated embodiment is a paraffin, carbowax, tallow, candelilla, ceresin, beeswax, or other natural or synthetic wax or wax-like substance that can be used conventionally in making candles. In the illustrated embodiment the trap 14 is of the type conventionally used when the selected animal to be attracted is a rodent, such as a rat or mouse.

The attractant food substance in the illustrated embodiment directed to rodents is one of the many favored by rodents, such as a nut-fruit or the like, ground, milled, or otherwise processed into a particulate, the particles being of small enough size to make the composite bait material flowable when the hardening substance melts into a liquid due to application of heat. Smaller particles remain suspended in the liquid hardening substance while larger particles tend to separate out. The use of smaller particles simplifies fabrication of a candle of composite bait material. For example, less frequent stirring of a hot liquid composite bait material is required when smaller particles are used. Additionally, in this embodiment the larger particles tend to char and burn when the candle is lit. It has been found that use of smaller particles reduces this charring problem, and so larger particles are less desirable in light of these considerations.

If larger particles tending to settle out of suspension are used, the aforementioned problems can be mitigated by using a casting method wherein the candle of this embodiment is cast on its side, as opposed to other fabrication methods involving a vertical orientation. In such a method, the longitudinal axis of the candle is oriented horizontally, and settlement of larger attractant particles during casting will result in a uniform dispersion of particles along the entire length of such a candle. The particles will be located in a longitudinal area located near the side of the candle that was oriented downward during casting. Without such an orientation, heavy settling particles could be concentrated at one end of a vertically cast candle for example. The longitudinal disposition of the attractant particles gives uniform bait consistency along the length of the candle of this embodiment and provides some separation from the wick, helping to minimize charring.

The longitudinal disposition of heavier particles separating from suspension will have analogous applications in other embodiments where an elongated bait compound configurations will be used, including those described below.

The attractant food particles can be formed of various substances. Nuts have been found to be very effective. Walnuts, almonds, pistachios, pecans, peanuts, and cashews, for example, might be used. As an alternative, peanut butter can be used. Also, particles of ground or milled grains, legumes, tuberous plants, or seeds, for example sunflower seeds, canary grass seeds, dried peas, dried beans, sweet potatoes, wheat, corn, barley or oats may alternatively be used. Other embodiments include dried and ground alfalfa, chocolate, lentils and coconut, fish or animal meat, as well as mixtures of various portions of nuts, grains, legumes, seeds, and these other substances, for example.

Selection of the attractant substance is largely a factor of cost and the particular preferences of the selected animal desired to be trapped. Milled nuts work well in paraffin as the nut oils readily mix and blend with the paraffin.

As an alternative to food substances, in another embodiment substances having scents attractive to the selected animal may be employed. For example, a substance smelling like peanuts could be substituted for peanuts. However, it is preferable to have a substance in the composite bait material that the selected animal, such as a rodent in the illustrated embodiment, will bite repeatedly so as to more reliably trip the trigger 12 of the trap 14. It has been found that a particulate form of a food substance works well for this purpose in this embodiment, though in other embodiments where the binder is edible a scent may be all that is required to attract the selected animal.

The candle 10 of composite bait material can be made conventionally, for example by a conventional molding, extruding or dipping process (not shown). Particles of the attractant food substance are added to the hardening substance heated so as to be in liquid form, such as heated wax. After mixing, a suspension of the attractant substance in the wax results. The particles of attractant food substance, if significantly different in density than the liquid wax or other solidifying substance, will tend to separate out of suspension over time. As can be appreciated, a mixture of the liquid solidifying substance and the particulate animal attractant food substance may require further mixing or agitation prior to and during the fabrication of the candle 10. As mentioned, the amount and timing of such further mixing depends on the particle size of the attractive food substance, as well as the relative densities of the liquid wax binder or other solidifying substance and the animal attractive substance. After mixing the hardening substance cools and solidifies as the composite bait material is formed into the desired shape in accordance with conventional candle making methods.

In use, the candle is lit and placed over the trigger while liquified composite bait material drips down thereon. After the hardening substance is cooled the particles of food substance are bound together and firmly attached to the trigger 12. It has been found that a "hard" paraffin having a melting point in excess of about 160° fahrenheit (as opposed to "soft" paraffins melting in the 120° to 140° range) works well in the illustrated embodiment. As the hardening substance solidifies sooner, it is easier to build up a mass of bait material on the trigger 12 in a shorter time using materials with a higher melting point.

It has also been found that a paraffin wax binder has a preservative effect allowing the bait material to be effective for a longer period, and this property is advantageous as it allows a longer period of time between freshening bait; this reduces the effort required in maintaining a trap or a number of traps in a good condition to catch animals. However, in this and all other embodiments discussed herein, the composite bait material should be stored in an air-tight container, such as a plastic bag (not shown) prior to use to maximize freshness.

Alternative to a candle 10 to drip composite bait material onto a trigger 12 of a trap 14, FIG. 2 illustrates another embodiment, where a small button candle 30 is placed upon the trigger 12 of a trap 14 and lit. Its purpose is to melt and reform onto the trigger as a mass of composite bait material included with and adhering to the trigger. The composition of the composite bait material from which the candle is formed is identical to that described above. However, in this embodiment it is necessary to disable the trap prior to rebating with another button candle as the candle is placed upon the trigger, disturbing it.

Referring now to FIG. 3, in another embodiment a cylinder 32 of composite bait material is formed conventionally, for example by a molding or extruding process. Heat is applied to the cylinder, for example by a butane cigarette lighter (not shown), a hot air gun (not shown), a propane torch (not shown) or other heat source. As shown in FIG. 4, a hot iron 34 may be used, and liquified composite bait material is dripped onto a trigger 12 as described above to bait a trap 14. Other types of hot irons, such as soldering irons (not shown) could be used instead of the type illustrated.

In a further embodiment, the cylinder 32 of composite bait material may be formed using another hardening substance for a binder material, such as a thermoplastic polymeric resin for example. Materials of this type are in common use in "hot glue guns" and a composite bait material as described above using such a polymer binder could be formed into a cylinder 32 adapted to fit in such a hot glue gun. High temperature waxes and paraffins could also be used, for example. As shown in FIG. 5, a conventional hot glue gun 36 could be used to apply liquid composite bait material 38 to the trigger 12 of a trap 14 for controlling rodent populations, for example. As with the use of a hot iron 34 mentioned above, the use of a hot glue gun 36 does not involve an open flame, which may be advantageous in situations where a risk of fire or explosion (such as controlling rodents in a grain elevator facility) is presented.

However, since electricity is required for conventional hot glue gun 36 operation, traps 14 may have to be baited at a location near a power source and then transported to the respective locations where they are to be placed and then set. Since the composite bait material 38 adheres to the trigger 12 this is not any more inconvenient than transporting the traps unbaited. This is true of all the embodiments described herein, the composite bait material of the invention makes baiting a number of traps at a single location possible, without setting them, and thereafter distributing them to desired locations and setting them at those locations. The later operation of distributing and setting the traps can be a considerable time after the baiting operation, is an advantage of the bait compound of the described embodiment of the invention is that is has been found to be effective for many weeks, even months after application to a trap.

Other types of hardening substances could be used as a binder in the composite bait material besides those dependent on temperature discussed above. For example, a binder incorporating a solvent which evaporates in the ambient conditions in the location in which the trap 14 is to be used could be employed, the composite bait material hardening as the solvent evaporates. In this regard water soluble binder substances may be used. Also, colloidal suspensions of adhesive materials could be used as a hardening substance, hardening as the substance drys. These binder materials include such solute substances as: soluble silicates; natural and synthetic rubbers and elastomers; natural and synthetic gums and resins, including gum arabic and other soluble polymers; glucose and mucilage; Zinc Stearate; asphalts; and pitches. Colloidal materials include: emulsions of polymers, including latexes; animal and fish derived glues, including casein and blood glues; and vegetable derived glues, such as soybean starch cellulosics. Many common household glues and library pastes are suitable, provided they can be thinned or thickened as needed and that they remain amorphous during drying so that the effects of any shrinkage due to evaporation of the solvent in the first case or the fluid in which the colloid is originally suspended in the second will be mitigated and the composite bait material will not pull away from the trigger as it dries.

Figure 6:
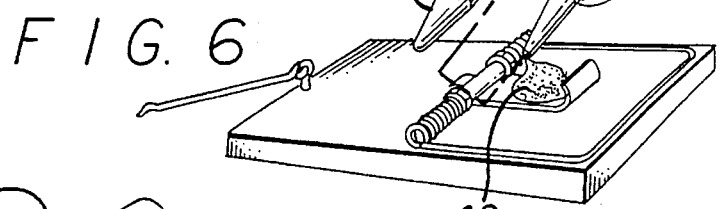
FIG. 6 is a perspective view of an embodiment of the invention where the composite bait material is applied from a sealed container and hardens without heat.

Referring to FIG. 6, i.e. a composite bait material 42 using such a binder could be pre-mixed and stored in sealed re-sealable containers 44 for use, such as squeezable tube containers having a cap 46, or wide-mouth containers (not shown) from which the composite bait material can be dispensed by use of a spatula (not shown) for example. Alternatively, referring to FIG. 7, the attractant food substance and the solute binder could be stored in a dry powder form 50 and the composite bait material prepared as needed by addition of an appropriate amount of solvent 54 (for example water), or other liquid in which colloids can be suspended, to an appropriate amount of dry powered binder and attractant substance. In either case a preservative may be required to keep the animal attractant substance fresh.

Alternatively, hardening substances 50 which harden by means of a chemical change could be used, such substances being usually characterized by the mixing of two or more substances 54, 50 to make use of a chemical interaction between them, or one or more constituent parts of each of them. Since the hardening of such substances occurs upon mixing, at least two separate components of such a hardening substance must be separately stored prior to use. Of course the animal attractant food substance could be combined with one or the other component of the hardening substance depending on compatibility over the anticipated storage time.

Figure 7:
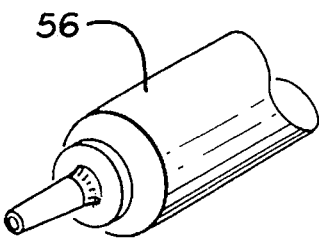
FIG. 7 illustrates a further embodiment where the composite bait material is prepared by adding a liquid.
Figure 8:
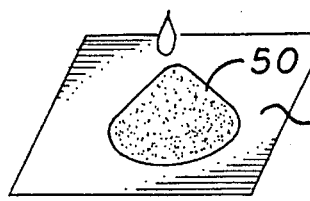
FIG. 8 illustrates application of prepared composite bait material to a trap.

Examples of such hardening substances 50 include two-part epoxies, which harden after using, as well as a number of cementenous materials, including those that harden after or by means of a hydrolization or hydration process. More specifically, an example of such a cementenous material is a flour of a substance high in starch, such as wheat flour or other flours made from the cereal grains, rice, oats, and the like, in combination with salt. This, with the addition of water 54 can form a hardening substance. If necessary, additional starch material from other sources (not shown) could be added. In another example, the dry components of common library paste are mixed with a dry particulate food substance to form a dry mixture 50 which can be measured out as required, for example being poured upon a sheet of cardboard 52. A measured amount of water 54 is then added from a water dispenser 56. Referring to FIGS. 7 and 8, after mixing the dry mixture 50 with the added water 54 a flowable paste 58 is formed which is then applied to the trigger 12 of a trap 14 to be set, for example by use of a small spatula 60.

Additional hardening substances of this type include portland cement, phosphate cement, mortar, plaster, or gypsum in combination with water. Also, a combination of flour and salt, when mixed with vegetable oil, sets up to form a hardened cementenous material after mixing.

Referring again to FIG. 6, another type of hardening substance that could be used in the composite bait material 42 is one of the class of materials that interact chemically with one or more atmospheric components such as water. For example, polymers which cross-link when exposed to water in the air, such as cyanoacrylates, could be employed. As will be appreciated, compounds of attractive food substances and such hardening substances may require storage in a sealed container 44, 46 after their preparation, and inhibitors, such as are well known for these materials, can be added to prolong their shelf life. Some may further require that the amount of air within the sealed container be kept at a minimum, indicating use of a squeeze dispensing tube for this purpose.

From the forgoing it will be appreciated that the composite bait material and method of use of the present invention allows improved control of selected animal populations by trapping. Improved adhesion and/or interlocking with a trap trigger 12 by a mass 18 of composite bait material lessens the incidence of bait stealing, and, combined with the stiffness of the hardened bait mass, more effectively transfers forces arising from biting, chewing or other contact by a selected animal to the trigger for better actuation of the trap 14 and increased success in trapping. Moreover, as traps baited with a composite bait material according to the present invention need freshening less often, and can be more readily transported without disengagement or deformation of a mass of bait on a trigger than conventional bait composite materials, the composite bait compound of the invention allows more convenient trapping of selected animals.

While several particular forms of the invention have been described, it will be apparent that various modifications can be made without departing from the spirit and scope of the invention.

What is claimed is:

1. A method of baiting an animal trap in trapping a selected animal, comprising:

mixing a food substance attractive to a selected animal with a hardening substance adapted to be flowable when mixed with said attracted food substance, but hardened when exposed to air at ambient temperatures at a selected location where said animal trap will be located, to form a composite bait material;

heating at least said hardening substance to ensure that said composite bait material assumes a liquified state;

applying said liquified composite bait material onto a trigger of said animal trap so said composite bait material conforms and adheres thereto;

allowing said composite bait material to harden;

setting said animal trap;

whereby improved force coupling between said composite bait material and said trigger gives improved triggering of the trap when an animal disturbs said bait composite material.

2. The method of baiting an animal trap of claim 1, further comprising the step of:

forming a desired shape of solidified composite bait material by allowing said flowable composite bait material mixture to cool and transform into a solid state in a desired shape.

3. The method of baiting an animal trap of claim 2, wherein:

said forming step includes configuring said composite bait material mixture into a candle adapted to drip composite bait material onto a desired location on said trap;

said heating step includes lighting said candle to melt said candle; and said applying step includes dripping said composite bait material onto said trigger to form a mass of composite bait material thereon.

4. The method of baiting an animal trap of claim 1, further comprising the step of:

forming said composite bait material into a pellet adapted to fit into and function in a hot-melt glue gun adapted to drip composite bait material onto a desired location on said trap;

wherein said applying step includes dripping said composite bait material onto said trigger to form a mass of composite bait material thereon.

5. The method of baiting an animal trap according to claim 1, wherein said attractive food substance comprises at least one substance derived from a food source selected from the group consisting of: nuts, seeds, grains, and legumes.

6. The method of baiting an animal trap according to claim 1 wherein the animal attractant food substance comprises a substance derived from a food source selected from the group consisting of walnuts, almonds, pistachios, pecans, peanuts, sunflower seeds, coconut, chocolate, alfalfa, cashews, and oats, wheat, and corn, rye, rice, and millet.

7. The method of baiting an animal trap according to claim 5 wherein said hardening substance is a wax suitable for candle making and said attractant food substance includes a particulate comprising milled nuts.

\* \* \* \* \*